United States Patent
Crouther et al.

(10) Patent No.: US 11,369,740 B2
(45) Date of Patent: Jun. 28, 2022

(54) MEDICAL DEVICE ANTENNA SYSTEMS HAVING EXTERNAL ANTENNA CONFIGURATIONS

(71) Applicant: ABBOTT DIABETES CARE INC., Alameda, CA (US)

(72) Inventors: Nathan C. Crouther, San Francisco, CA (US); Marc B. Taub, Mountain View, CA (US); Lei He, Moraga, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 441 days.

(21) Appl. No.: 16/450,655

(22) Filed: Jun. 24, 2019

(65) Prior Publication Data
US 2020/0147304 A1 May 14, 2020

Related U.S. Application Data

(63) Continuation of application No. 14/876,185, filed on Oct. 6, 2015, now Pat. No. 10,369,282, which is a
(Continued)

(51) Int. Cl.
| | |
|---|---|
| *A61B 5/145* | (2006.01) |
| *A61M 5/172* | (2006.01) |
| *A61M 5/142* | (2006.01) |
| *H01Q 1/22* | (2006.01) |
| *H01Q 1/27* | (2006.01) |

(Continued)

(52) U.S. Cl.
CPC ........ *A61M 5/172* (2013.01); *A61B 5/14532* (2013.01); *A61B 5/6833* (2013.01); *A61M 5/14248* (2013.01); *A61M 5/1723* (2013.01); *H01Q 1/2208* (2013.01); *H01Q 1/273* (2013.01); *H01Q 5/48* (2015.01);
(Continued)

(58) Field of Classification Search
CPC .......... A61M 5/142; A61M 2205/3569; A61M 2230/201; A61M 2205/3592; A61M 5/14248; A61M 5/172; A61M 5/1723; H01Q 1/22; H01Q 1/27; H01Q 1/2208; H01Q 5/48; H01Q 1/273; A61B 5/6833; A61B 5/14532
See application file for complete search history.

(56) References Cited

U.S. PATENT DOCUMENTS

| | | |
|---|---|---|
| 5,057,106 A | 10/1991 | Kasevich et al. |
| 5,861,019 A | 1/1999 | Sun et al. |

(Continued)

*Primary Examiner* — Eric J Messersmith
(74) *Attorney, Agent, or Firm* — One LLP

(57) ABSTRACT

A medical device includes an antenna external to a case, package, or encapsulant for the electronic systems of the medical device. In one embodiment, a diabetes infusion pump is enclosed within a metal case, the pump including a processor and a communication module for wireless communications. An antenna is disposed in the delivery tubing of the pump outside the case with an antenna feed interconnecting the external antenna with the internal communication module. In another aspect, a thin film antenna is formed on the outer surf ace of the case in which a physiological parameter sensor, such as a glucose sensor, is enclosed. Multiple antennas may be used for communications on different frequencies.

20 Claims, 11 Drawing Sheets

Related U.S. Application Data continuation of application No. 12/790,182, filed on May 28, 2010, now Pat. No. 9,184,490.

(60) Provisional application No. 61/182,678, filed on May 29, 2009.

(51) Int. Cl.
*A61B 5/00* (2006.01)
*H01Q 5/48* (2015.01)

(52) U.S. Cl.
CPC ............... *A61M 2205/3569* (2013.01); *A61M 2205/3592* (2013.01); *A61M 2230/201* (2013.01)

(56) References Cited

U.S. PATENT DOCUMENTS

| | | | |
|---|---|---|---|
| 6,161,036 A | 12/2000 | Matsumura et al. | |
| 6,175,752 B1 | 1/2001 | Say et al. | |
| 7,206,630 B1 | 4/2007 | Tarler | |
| 2002/0058906 A1 | 5/2002 | Lebel et al. | |
| 2002/0080074 A1 | 6/2002 | Wang | |
| 2002/0118142 A1 | 8/2002 | Wang | |
| 2004/0222924 A1 | 11/2004 | Dean et al. | |
| 2004/0229665 A1* | 11/2004 | Mori | H01Q 1/243 455/575.1 |
| 2005/0096513 A1 | 5/2005 | Ozguz et al. | |
| 2005/0182389 A1 | 8/2005 | LaPorte et al. | |
| 2005/0197540 A1 | 9/2005 | Liedtke | |
| 2005/0197654 A1 | 9/2005 | Edman et al. | |
| 2006/0038725 A1 | 6/2006 | Tikhov et al. | |
| 2007/0049806 A1 | 3/2007 | Adams et al. | |
| 2008/0119707 A1 | 5/2008 | Stafford | |
| 2008/0198082 A1* | 8/2008 | Soler Castany | H01Q 1/38 343/893 |
| 2009/0228074 A1* | 9/2009 | Edgell | H01Q 1/40 607/60 |
| 2009/0270948 A1* | 10/2009 | Nghiem | A61N 1/37229 607/60 |
| 2009/0315787 A1* | 12/2009 | Schatzle | H04R 25/554 343/788 |
| 2010/0019985 A1* | 1/2010 | Bashyam | A61N 1/37518 343/873 |
| 2010/0149042 A1 | 6/2010 | Utsi et al. | |
| 2010/0161002 A1* | 6/2010 | Aghassian | H01Q 13/10 607/60 |
| 2010/0188292 A1* | 7/2010 | Rutfors | H01Q 9/0421 343/700 MS |
| 2010/0255892 A1* | 10/2010 | Harada | H01Q 9/36 455/575.1 |
| 2011/0022121 A1 | 1/2011 | Meskins | |
| 2011/0063184 A1* | 3/2011 | Furumura | G06K 19/07783 343/856 |

* cited by examiner

MEDICAL DEVICE ANTENNA SYSTEMS HAVING EXTERNAL ANTENNA CONFIGURATIONS

RELATION TO OTHER APPLICATIONS

The present application is a continuation of U.S. patent application Ser. No. 14/876,185, filed Oct. 6, 2015, which is a continuation of U.S. patent application Ser. No. 12/790,182, filed May 28, 2010, now U.S. Pat. No. 9,184,490, which claims the benefit of U.S. Provisional Application No. 61/182,678, filed May 29, 2009, all of which are incorporated herein by reference in their entirety for all purposes.

BACKGROUND

The invention relates generally to wireless data transmission and more particularly, to antenna systems that are integrated into medical equipment.

Medical devices often include wireless communication features requiring an antenna associated with each device that transmits or receives wireless communications. Existing medical devices sometimes include antenna elements that are located in medical device packages or cases. However, such antennas generally occupy significant areas of the relevant package or the embedded electronics, and may offer sub-optimal performance due to interference and attenuation associated with the components and packaging within which or with which they are located. As such, they are unable to provide reliable wireless communications yet they significantly increase the overall size of the medical devices.

It is also desirable to make medical devices that must be worn or carried by a user as small and as light as possible for user convenience. This has the added benefit of making the medical devices less intrusive and therefore more likely to be used by the patients. Spreading features among the components can achieve the goal of not making any one component large and heavy. Additionally, some medical devices may be inherently unfriendly to wireless communications due to their nature. For example, some diabetes medication pumps have metal cases for durability and to make them water tight. The metal case can significantly interfere with wireless communications where the antenna is inside the case. It would be desirable to locate an antenna or antennas for wireless communications outside the metal case yet be sure that the antenna is capable of efficiently functioning with the internal communications module and circuitry.

In sum, there is a need for an antenna and related systems that may adequately enable wireless communications between medical devices by, for example, utilizing an external antenna constructed for optimal implementation with medical device packages.

Hence those skilled in the art have recognized a need for an improved antenna system that will enable more reliable wireless communication between a medical device and another device. A need has also been recognized for antennas that provide a larger radiation pattern with an omni-directional pattern being very desirable. A further need has been recognized for maintaining medical devices small while at the same time allowing them to have reliable wireless communications with other devices through the use of efficient antenna structures. The invention fulfills these needs and others.

SUMMARY OF THE INVENTION

The invention is directed to medical devices having external antennas for reduced size of the device and more reliable wireless communications. In one aspect there is provided a medical device having wireless communication capability for data transfer with a host device, the medical device comprising a processor configured to control at least one function of the medical device, a wireless communication module configured to communicate at a first frequency, the communication module being in operational data connection with the processor, a case enclosing the processor and the wireless communication module, the case having an outer surface and defining an inside space within which the processor and wireless communication module are located, and an outside space within which the outside of the case and surrounding areas and objects are located, the outer surface of the case residing in the outside space, an antenna located in the outside space configured to efficiently communicate at the first frequency, and an antenna feed interconnecting the antenna with the wireless communication module, whereby the antenna provides a transducer for wireless data communication between the processor and a host device.

In another more detailed aspect, the medical device further comprises a pump located in the inside space, the pump being under control of the processor, a delivery tube through which the pump forces a medical fluid to flow, the delivery tube having a first end located in the inside space and a second end located in the outside space, wherein, the antenna feed and antenna are co-located with the delivery tube. In another aspect, the antenna feed co-located with the delivery tube is capacitively coupled to the communication module in the inside space. In yet another, the antenna feed co-located with the delivery tube is inductively coupled to the communication module in the inside space.

In yet further aspects, the delivery tube comprises a tube wall and a lumen through which fluid flows, and the antenna feed and the antenna are formed as part of the tube wall. The delivery tube comprises a tube wall and a lumen through which fluid flows, and the antenna feed and the antenna are formed as part of the tube wall through co-extrusion with the delivery tube. The delivery tube comprises a tube wall and a lumen through which fluid flows, and the antenna feed and the antenna are formed as a conductive polymer path embedded and co-extruded within a wall of the tube. The delivery tube comprises a tube wall and a lumen through which fluid flows, and the antenna feed and the antenna are printed on an outside surface of the tube. The delivery tube comprises a tube wall and a lumen through which fluid flows, and the antenna feed and the antenna include a conductive portion wound around a portion of the tube. The delivery tube comprises a tube wall and a first lumen through which fluid flows and a second lumen, separate from the first lumen, and the antenna is located within the second lumen of the delivery tube.

In other more detailed aspects, the antenna is formed on the outer surface of the case and the antenna feed interconnects the communication module at a point in the inside space to the antenna at a point in the outside space. The antenna is formed in a meandering pattern.

In yet further aspects, an adhesive patch is attached to the case at one surface and having a second surface on which is located an adhesive suitable for holding the patch and the medical device to the skin of a user, wherein the antenna comprises conductive wires woven into a layer of the adhesive patch. The device includes an adhesive patch with a first side and a second side wherein the antenna is formed on the first side of the adhesive patch, wherein the case is attached to the first side of the adhesive patch, and the second side of the adhesive patch comprises an adhesive surface configured to adhere to skin of a user.

In more aspects, the medical device further comprises a sensor located in the inside space, the sensor being operatively connected with the processor wherein the case is an encapsulant, wherein the antenna is formed on the outer surface of the encapsulant, and wherein the antenna feed interconnects the communication module at a point in the inside space to the antenna at a point in the outside space. Additionally, the medical device further comprises a second antenna located in the outside space configured to efficiently communicate at a second frequency, and a second antenna feed interconnecting the second antenna with the wireless communication module.

In yet further aspects, there is provided a medical device having wireless communication capability for data transfer with a host device comprising a processor, a wireless communication module configured to communicate at a first frequency, the communication module being in operational data connection with the processor, a medical device comprising a case enclosing communication circuitry and a processor, wherein the communication circuitry and the processor are communicatively coupled, a sensor configured to sense a physiological parameter and provide sensor data to the processor, a case enclosing the processor, the sensor, and the wireless communication module, the case having an outer surface and defining an inside space within which the processor, sensor, and wireless communication module are located, and an outside space within which the outside of the case and surrounding areas and objects are located, the outer surface of the case residing in the outside space, a thin film antenna located in the outside space configured to efficiently communicate at the first frequency, and an antenna feed interconnecting the antenna with the wireless communication module, whereby the antenna provides a transducer for wireless data communication between the processor and a host device.

In more detailed aspects, the thin film antenna is formed on a surface of the case. The antenna is printed on an outside surface of the tube. The antenna is formed in a meandering pattern. The sensor includes a glucose sensor.

Other features and advantages of the invention will become more apparent from the following detailed description of preferred embodiments of the invention, when taken in conjunction with the accompanying exemplary drawings.

BRIEF DESCRIPTION OF THE DRAWINGS

The accompanying drawings, which constitute a part of this specification, illustrate various implementations and aspects of the present invention and, together with the description, explain the principles of the invention. In the drawings:

FIG. 7c is a top view of the antenna of FIG. 7a;

DETAILED DESCRIPTION OF PREFERRED EMBODIMENTS

Many medical devices, such as sensors and pumps, involve wireless communication. This is particularly true for sensors that measure physiological parameters such as glucose, and pumps that deliver insulin, pramlintide, glucagon, or other pharmacological or nutritional agents. Pumps typically couple to an external infusion set, often disposable, that includes an external tube through which fluids are received or delivered. The tubing used to deliver or receive the fluids provides an excellent opportunity to improve antenna design over conventional antennas that may be used in such medical devices. A similar situation can also exist for other medical devices where external antennas may be integrated into an external portion of the medical device, where an external space for mounting an antenna can be provided, or when the medical device is used with an external component where integration of an antenna is feasible. Such improved antenna designs may be implemented in a number of ways that provide improvement over existing systems.

Figure 1:
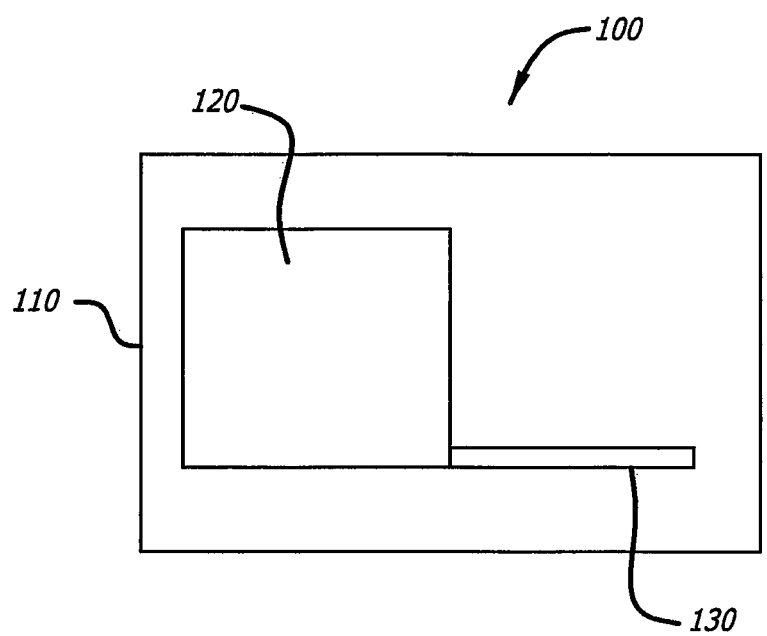
FIG. 1 is a block diagram of a medical device having internal functional modules and an internal antenna near those modules.

In the following description, like reference numerals are used to refer to like or corresponding elements in the different figures of the drawings. Referring now to the drawings with more particularity, FIG. 1 illustrates in block diagram format the structure of several existing systems. FIG. 1 illustrates the basic structure of a medical device 100, which includes functional modules 120 in box form, an internal antenna 130 also in box form, and a case 110 surrounding all. Placement of the antenna inside the case 110 increases the size of the case 110, and may impair the ability to reliably transmit information in a desired direction, both because of interference provided by the surrounding case 110 and because of the potential for parts of the functional modules 120 to be placed between the antenna 130 and a desired radiation direction. Additionally, where the case or packaging 110 is metal, antenna function may be severely affected.

Figure 2A:
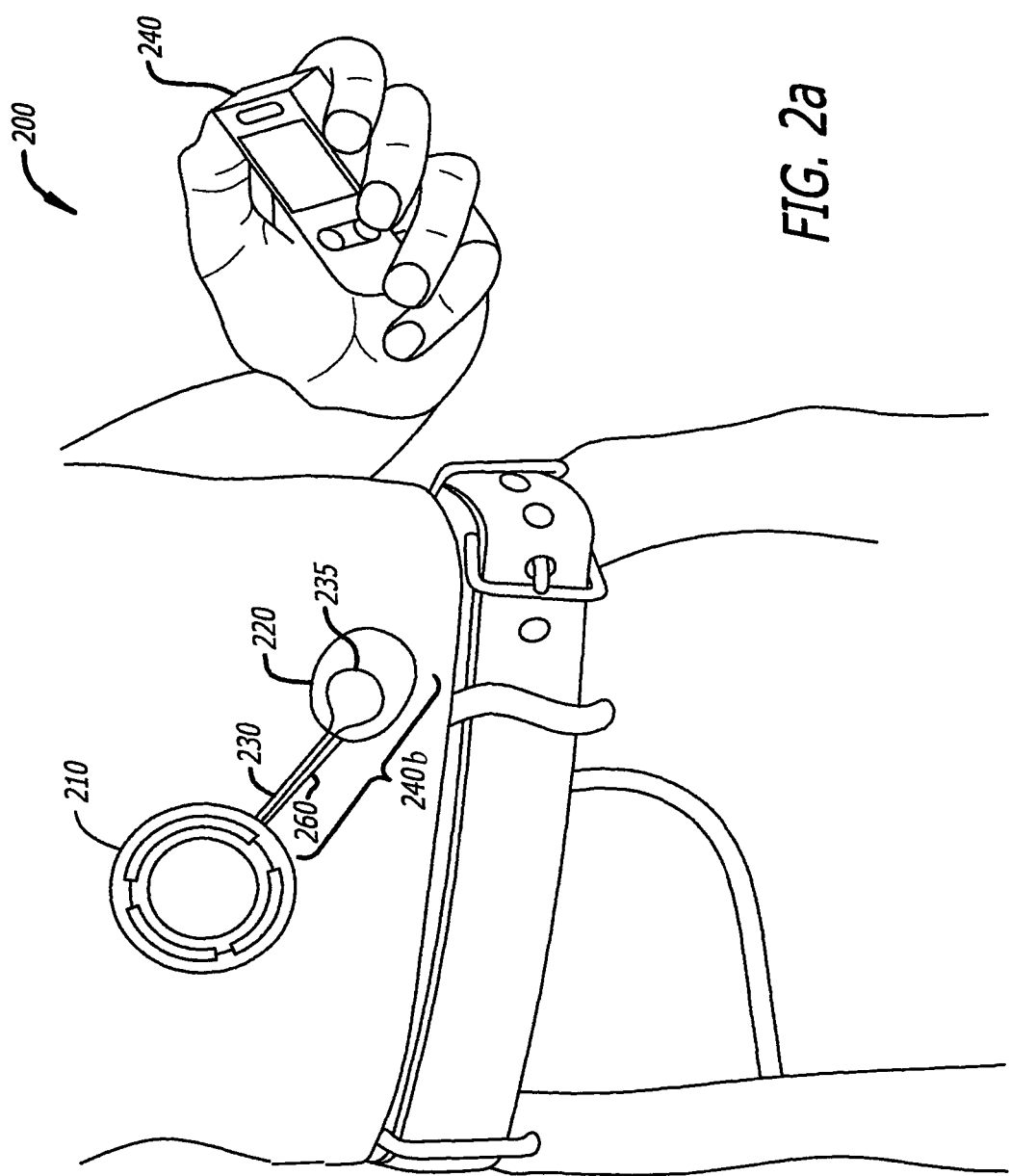
FIG. 2a shows a diabetes management system in which a delivery device attached to a patient's abdomen with an adhesive patch is connected through an infusion set to a delivery site on the patient's abdomen with a handheld control processor in wireless contact with the delivery device, the delivery device having an antenna for supporting wireless communication.

FIG. 2a illustrates use and structure of an embodiment of a system 200 consistent with certain aspects related to the present invention. On a very general scale, the system 200 shown in FIG. 2a comprises a portable handheld wireless electronic device 240, a medical device 210, a connector 230, a user interface device 220, and an antenna 260. The medical device 210 may be any medical device, such as for the delivery of medication to a user or for sensing a condition of the user, although it may or may not contain a sensor that creates data for transmission from the medical device 210 to the portable handheld electronic device 240 using the antenna 260. Although labeled in general terms as a "user interface device" 220, this device can also take different forms, one of which is an injection cannula 235, a sensor of a user physiological parameter such as glucose, or other device. The connector 230 may take different forms such as a delivery tubing, or electrical connector.

In this embodiment, the medical device 210, the connector 230 and the user interface 220 may be thought of as components of a particular medical system 200 for controllably delivering medication to a user. The antenna 260 functions with only one component of the system in this embodiment; i.e., the delivery device 210, but is mounted on another component (infusion set 240b) external to the delivery device of the system 200, as is discussed in more detail below. The user interface device in this embodiment comprises a medication injection cannula, although other devices may be used for the delivery of medication to the user at the delivery site, or for sensing a patient physiological parameter, or both.

Because the antenna 260 in this embodiment is external to the medical device 210, the "case" or "package" of the medical device 210 can be smaller. Also, the antenna 260 can have a greater size and take a variety of designs than would be possible for an antenna that is entirely confined to the inside of the case of the medical device 210. Such antennas, depending on their wavelength of operation, can be relatively large in comparison to the communication component operating with them. Thus, substantial space can be saved by locating them externally to the transmitter/receiver component with which they are connected.

In this embodiment, the antenna 260 may be attached to or structured as part of the infusion set 240b with which the medical device 210 is operating, as will be discussed in more detail below. In this case, the medical device 210 is configured in a case to which the infusion set 240b is attached and is an external device, so that the medical device 210 is separately located from the injection site of the user.

Separation of the medical device 210 from the injection cannula 235 allows for smaller packaging for both, and flexibility in configuration and placement on the body of a user. The length of the medical connector 230 (tubing of the infusion set 240b) also creates a trade off between flexibility of placement for the pump 210 and flexibility of placement of the injection cannula 235. When the pump 210 and the injection cannula 235 are both placed on the body of a user in close proximity, the delivery tubing 230 of the infusion set 240b may be shorter in length, with associated lower space and pumping requirements.

The portable handheld electronic device 240 may be any portable electronic device that includes a processing component, memory for electronic storage, and a wireless communication system. A wireless communication system (not shown) of the portable electronic device 240 may communicate with a communication component or module of the medical device 210 that transmits information using the antenna 260. According to some implementations, the portable handheld electronic device 240 may be connected to a network that allows upload and download of data to and from third party sources such as a user's doctor or a data storage and reporting service. The handheld device can take various forms one of which is envisioned as a smart phone. Of course, any of the antennas 260 set forth throughout this disclosure may be used in situations where the recipient device is not a portable handheld electronic device, as the transmissions can be sent to any stationary processing, or retransmission component configured to receive such signals.

Discussing the embodiment above in more detail, the medical device 210 may be an insulin pump for delivering insulin to a diabetic user. The insulin pump 210 and the injection cannula 235 of the diabetes infusion set 240b of FIG. 2a may each include an adhesive patch 220 that sticks to the skin of a user. This allows both the infusion pump 210 and the injection cannula 235 to be placed in a large variety of positions on the body of a user. The infusion set 240b comprises tubing 230 that interfaces between an insulin reservoir (not shown) contained in or attached to the infusion pump 210, to the injection cannula 220 to deliver that insulin internally to the user. The antenna 260 for this system that allows communication with the portable electronic device 240 is shown figuratively as being part of the tubing 230 of the infusion set 235. A communication component of the infusion pump 210 may be attached to the antenna 260 to transmit insulin delivery data to the portable electronic device 240. The data may then be stored or analyzed at the portable electronic device 240 or conveyed to another location. Additionally, in another embodiment, the handheld electronic device 240 may be used to wirelessly communicate programming instructions or other data to the pump through the antenna 260.

Figure 2B:
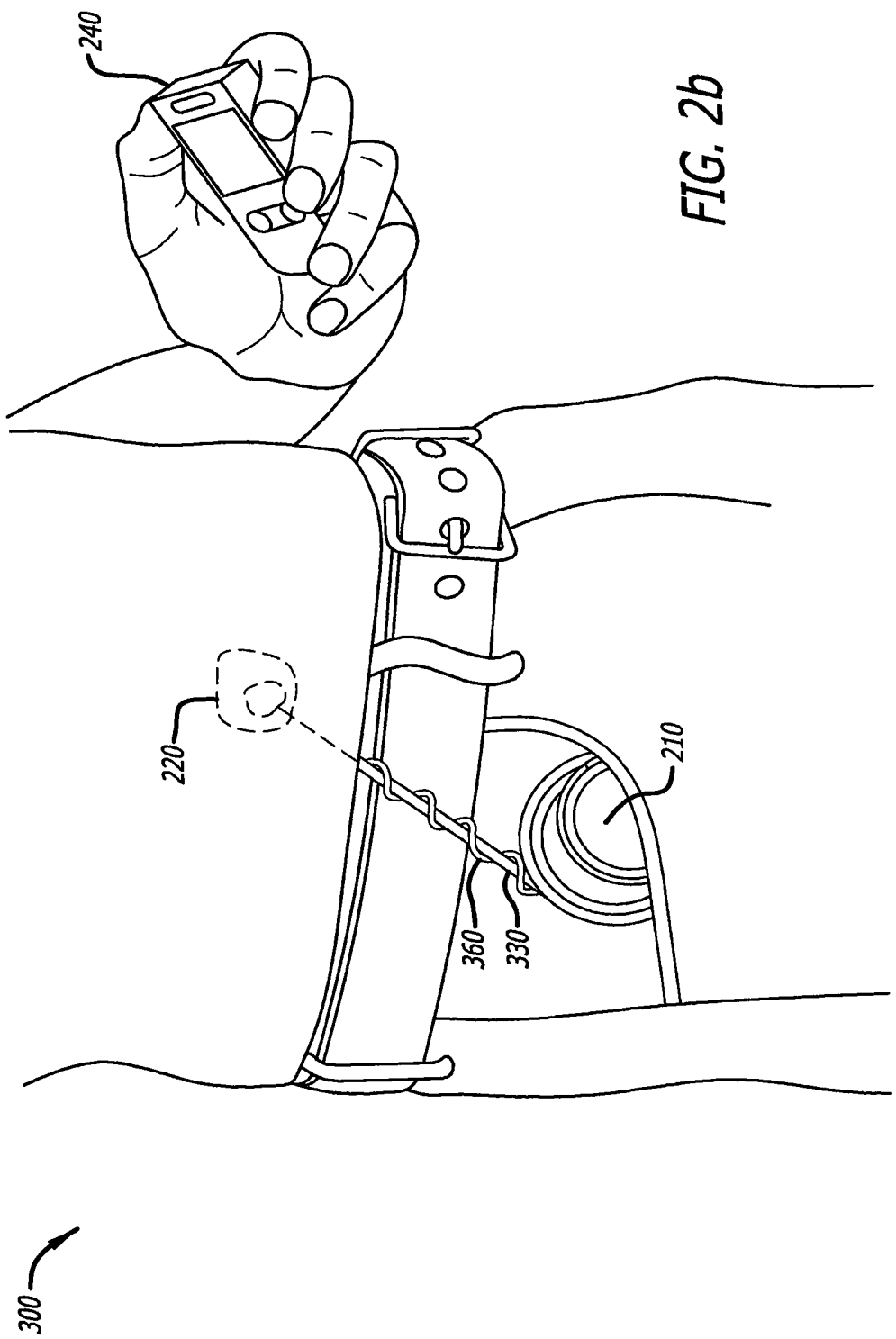
FIG. 2b is an illustration similar to that of FIG. 2a except that in this embodiment, the delivery device is located in the pocket of the user and uses an external antenna disposed about the infusion tubing for wireless communication with the handheld processor.

FIG. 2b illustrates a system 300 that differs somewhat from that of FIG. 2a. However, the system of FIG. 2b comprises a portable electronic device 240, a medical device 210, a medical connector 330, an antenna 360, and an injection cannula mounted to the user by an adhesive patch 220 similar to the system shown in FIG. 2a. The medical device 210 may simply be stored or carried as an attachment or in a pocket of an article of clothing of the user. In this case, the delivery tubing 330 may be significantly longer than the delivery tubing of FIG. 2a since the pump may not be located as closely to the injection site as in the system of FIG. 2a. This allows the pump 210 to be retained in the same location as the location of the injection cannula 235 is moved or is possibly replaced by interchangeable components of a medical device user interface 220. The antenna 360 of the medical connector 330 in FIG. 2b may only be included in or attached to a portion of the delivery tubing 330 medical connector 330, rather than running the entire length of the tubing, depending on the wavelength of operation. In this case, the antenna 360 is wrapped around the outside of the delivery tubing 330 in a helical pattern.

Figure 3B:
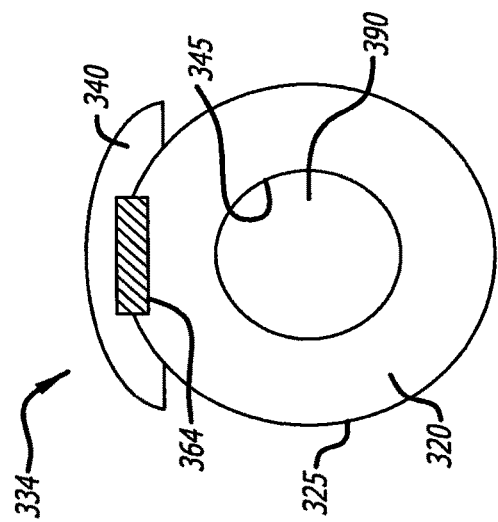
FIG. 3b is an end view of an embodiment of infusion set tubing with electrical conductors partially embedded into the outside surface of the wall of the tubing, the conductors being of use to form an antenna for wireless communications.
Figure 3A:
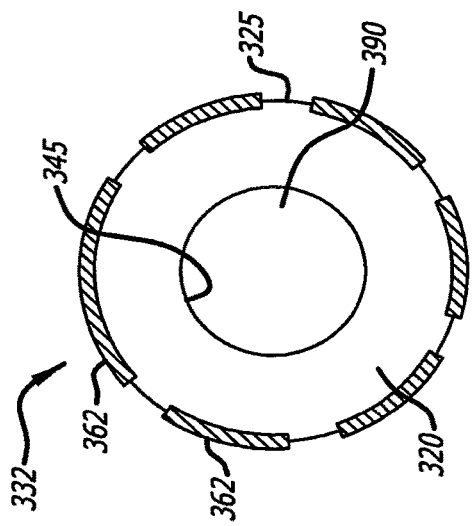
FIG. 3a is an end view of tubing used in a diabetes infusion set showing the inner and outer surface of the tubing wall with electrical conductors fully embedded in the tubing wall and covered by that wall for use as an antenna.

FIGS. 3a through 3e illustrate various embodiments of antennas integrated with delivery tubing. All FIGS. 3a through 3e show end-on, cross sectional views of medical tubing such as the medical delivery tubing of FIGS. 2a and 2b. All tubing of the several views has a lumen 390 and a tubing wall 320. The wall has an outer surface 325 and an inner surface 345. Referring first to FIG. 3a, the tube 331 has a lumen 390 for transporting a medical material. The antenna 361 of FIG. 3a is shown as including multiple strips of electrically conductive material completely embedded within the tube wall 320, although a single strip may be usable in another embodiment. The tubing 332 of FIG. 3b includes an antenna 362 made of multiple conductive strips that are partially embedded or attached to the outside surface 325 of the tube wall 320; however, in another embodiment, a single conductive strip may be used. In alternate arrangements for both the antenna 361 of FIG. 3a and the antenna 362 of FIG. 3b, the antennas may be single strips covering a small portion of the surface in a cut-out section of the tube wall 320, rather than the multiple strips covering a large portion of the outer surface, as shown in FIG. 3b.

Figure 3D:
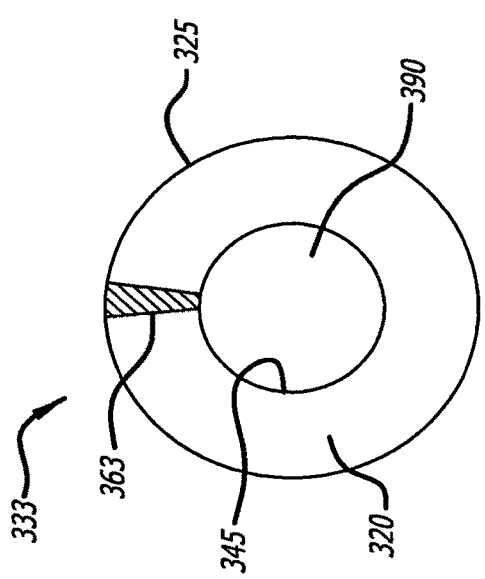
FIG. 3d is a further end view of tubing used in a diabetes infusion set in which an electrical conductor is partially embedded in the outer surface of the wall of the tubing but is covered by an added layer of the tubing.
Figure 3C:
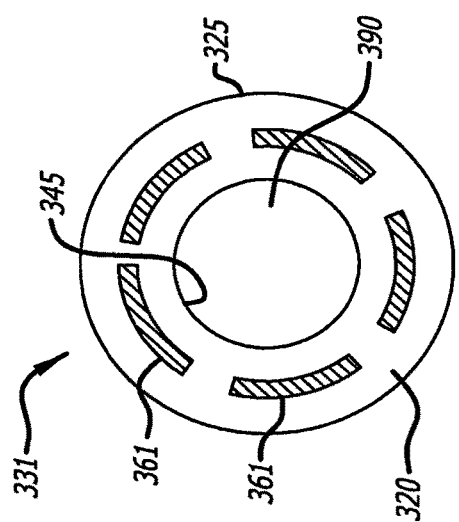
FIG. 3c is also an end view of tubing showing the existence of an electrical conductor embedded in the wall and forming a part of that wall of the tubing and being exposed at the outer wall for use as an antenna in supporting wireless communications.

The tube 333 of FIG. 3c includes an antenna 363 that is part of an entire section of the tube 320 from the outer surface 325 of the wall or near the outer surface to the inner surface 345 of the wall or near the inner surface, adjacent the lumen 390.

The tube 334 of FIG. 3d includes an antenna 364 which comprises a single strip of conductor embedded partially into the outer surface 325 of the tube wall 320. The antenna 364 is further covered by an additional encapsulating layer 340. The encapsulating layer 340 may be made of the same material as that of the tube 320, and may be manufactured such that tube 320 and encapsulating layer 340 are a continuous material, or they may be manufactured separately and as separate materials.

Figure 3E:
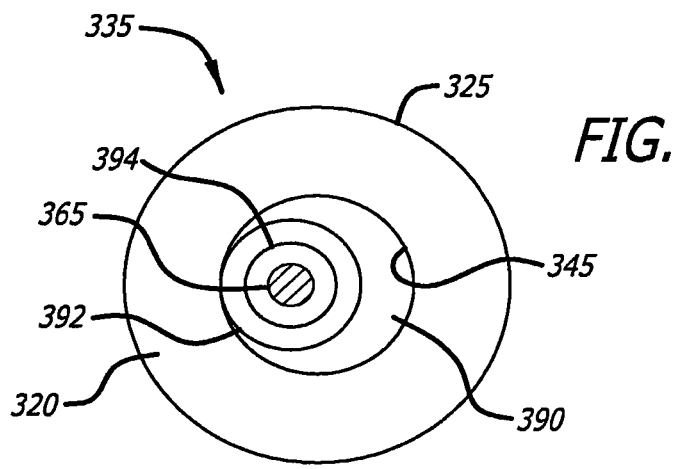
FIG. 3e is an end view of tubing used in a diabetes infusion set showing an electrical conductor placed in a second lumen of the tubing for use as an antenna to support wireless communications for a device using this tubing.

The tube 335 of FIG. 3e includes the antenna 365 in a second lumen. In this embodiment, the tube has two lumina, the first 390 for delivering medical material or fluids, such as insulin, and the second 392 for housing the antenna 365. In this embodiment, there is a common wall portion 394. Other arrangements may be made for two-lumina tubing; FIG. 3e presents only an example.

In another embodiment (not shown), the tube 335 may have a free-floating antenna 365 in the same lumen 390 as the medical fluid, wherein the antenna 365 is free floating within the lumen 390. The antenna 365 would be contained within the interior section 390 by the walls of the tube 320.

In FIGS. 3a-3e, the placement of the shown antenna may extend throughout a portion or the entire delivery tube. Alternately, different cross sections of a delivery tube may contain a different profile of the antenna and any encapsulant.

Figure 4A:
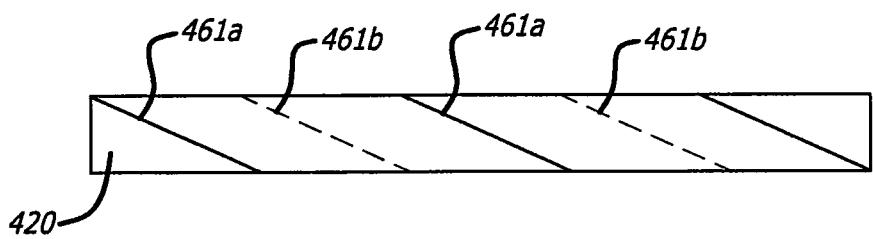
FIG. 4a is a side view showing an electrical conductor wrapped around the outer surface of a length of tubing used in a diabetes infusion set, the conductor is wrapped in a helical manner about the tubing and may be used as antenna to support wireless communications for a medical device using the tubing.
Figure 4B:
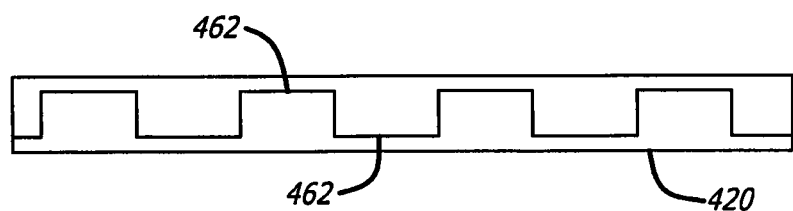
FIG. 4b is also a side view of tubing showing an electrical conductor mated to the outer wall of a length of the tubing by means of slots and ridges.

FIGS. 4a and 4b show additional implementations where the cross section of the delivery tube changes over the length of the medical connector. FIG. 4a shows a side view of a delivery tube such as medical connector 230 and 330 of FIGS. 2a and 2b, and shows a tube 420 with antenna 461. In FIG. 4a, the antenna 461 is wrapped around the tube 420 in a helical coil pattern such that antenna portion 461a is on the side of the perspective, and the antenna portion 461, shown as the dashed portion, is on the side of the tube 420 away from the perspective and behind the tube 420. FIG. 4b shows a medical connector including the tube 420 and an antenna 462. The antenna 462 of FIG. 4b is a meandering pattern formed completely on the perspective side of the tube 420.

Use of the above described antenna configurations with thin film printed antenna or other antenna offer superior radio frequency performance for wirelessly enabled pumps as opposed to internal antenna or single wire tube attached antenna. Use of the above described antenna configurations may also provide opportunity for material cost savings related to thin film conductors.

Figure 5A:
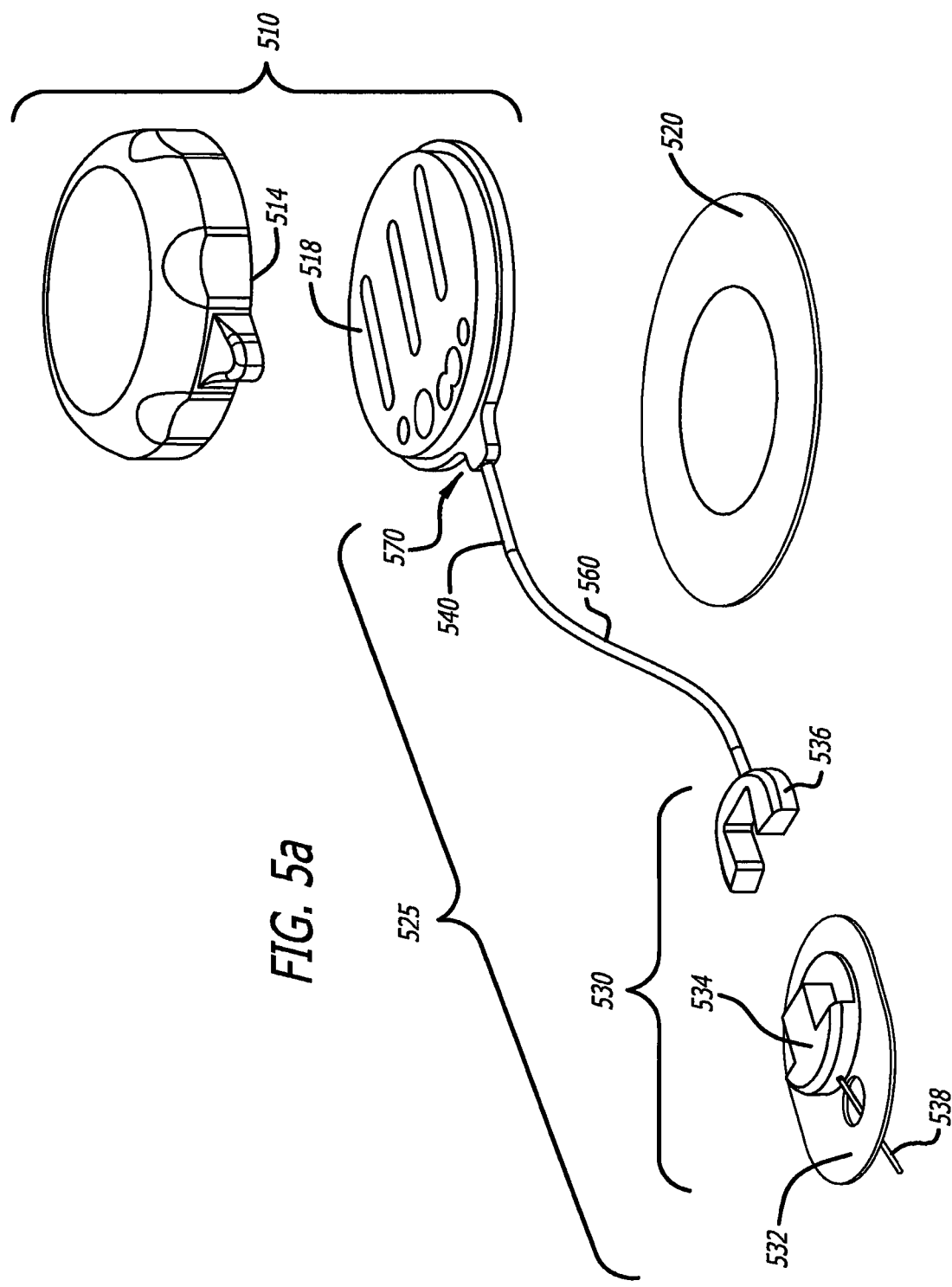
FIG. 5a provides detail of a medication delivery system that includes in this embodiment a medication pump and a diabetes infusion set, with the pump shown in an exploded view showing a case, a base with internal functional devices mounted thereon, and an adhesive mounting patch for locating the pump on a patient's body.

FIG. 5a illustrates a diabetes infusion pump 510 in exploded view, with an infusion set 525 having a length of delivery tubing 560 and an injection cannula 538 with a mounting adhesive patch 532. The delivery tubing is coupled to the injection cannula through a connector 530 having two disconnectable parts. A female portion 536 is releasably secured to a male portion 534 such that they may be disconnected from each other at the user's convenience. The user may wish to disconnect the connector when he or she is performing an activity where the pump should be removed. An example of such an activity is removing the insulin pump to take a shower.

The pump 510 includes a case 514, the functional modules of the insulin pump 518 including a wireless communication module, and an adhesive patch 520 attached to a surface of the pump 510 for mounting the pump 510 to the skin of a user. The antenna (not shown) is embedded within the delivery tubing 560 and may be attached to a communication module that is part of the insulin pump 518 at a point at or near where the delivery tubing attaches; i.e., at antenna interface 570.

Figure 5B:
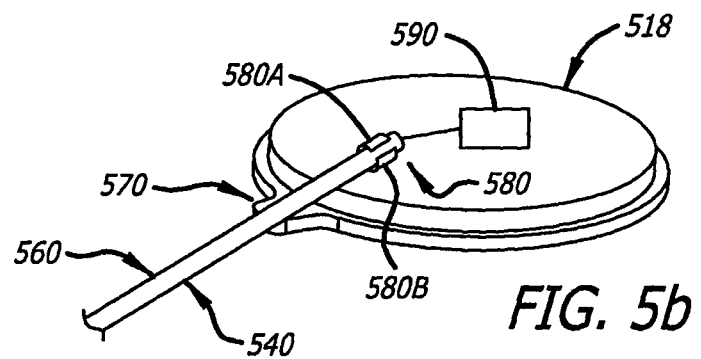
FIG. 5b is a partially schematic view of the pump case of FIG. 5a showing an antenna feed and antenna extending externally of the case for better operation and schematically shown as being terminated within the case and capacitively coupled to an internal communication component, the capacitive coupling, connection to the communication component, and the communication component itself being shown in schematic form.
Figure 5C:
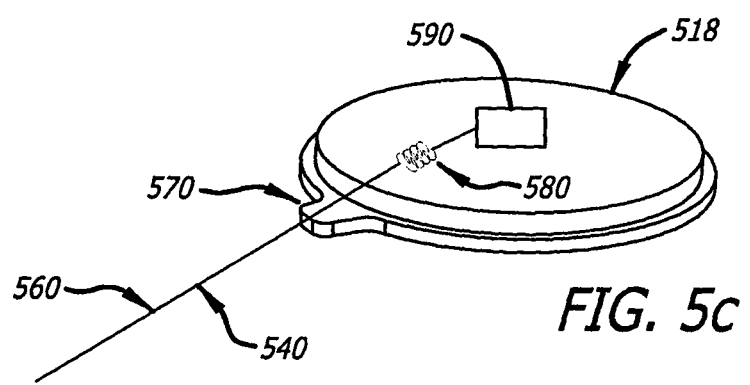
FIG. 5c is a schematic-type diagram similar to FIG. 5a in which the electrically conductive antenna feed is terminated within the case and inductively coupled to the communication component, the inductive coupling, connection to the communication component, and the communication component itself being shown in schematic form.

As shown purely by way of illustration and example in FIGS. 5*b* and 5*c*, the various external antennas 560 disclosed throughout may also be connected to their associated medical device by means of a capacitive or inductive coupling. FIG. 5*b* schematically shows details related to capacitively coupling 580 the antenna 560 to the communications module of the medical device 510 of FIG. 5*a*. The coupling element 580 is made up of capacitive plates 580A and 580B. This connection at the antenna interface 570 allows the antenna 560 which is attached to the delivery tubing 540 to deliver signals to and from the pump communication module 590 which is included inside the case 514 of the pump 518.

FIG. 5*c* shows an alternative means of coupling the antenna 560 to the communication circuitry 590. In this illustrative implementation, the antenna interface 570 includes a coupling element 580 which is schematically shown as an inductive coupling element. This coupling element 580 also allows the antenna 560 which is attached to the delivery tubing 540 to deliver signals to and from medical device wireless communication circuitry 590. As shown in this implementation, the coupling element is included inside the case 514 of the insulin pump 518.

Although not shown, direct electrical coupling to the antenna feed within the case of the medical device may also be performed. The tubing embodiments of FIGS. 3*b* and 3*e* have metallic antenna feed components 362 and 363 exposed at the outer surface of the tubing that would be mated with electrical conductors forming a part of the communication component inside the case of the medical device 510. A two-point contact connector can be used to simultaneously connect the fluid connection of the tubing and the antenna connection of the tubing within the pump 510. In a case where the infusion set comprises a built-in reservoir and a fluid connection is not necessary, the electrical connection would be made with an appropriate connector within the medical device. Such two-point connectors and other electrical connectors are well known to those of skill in the art and no further details are provided herein.

Figure 6:
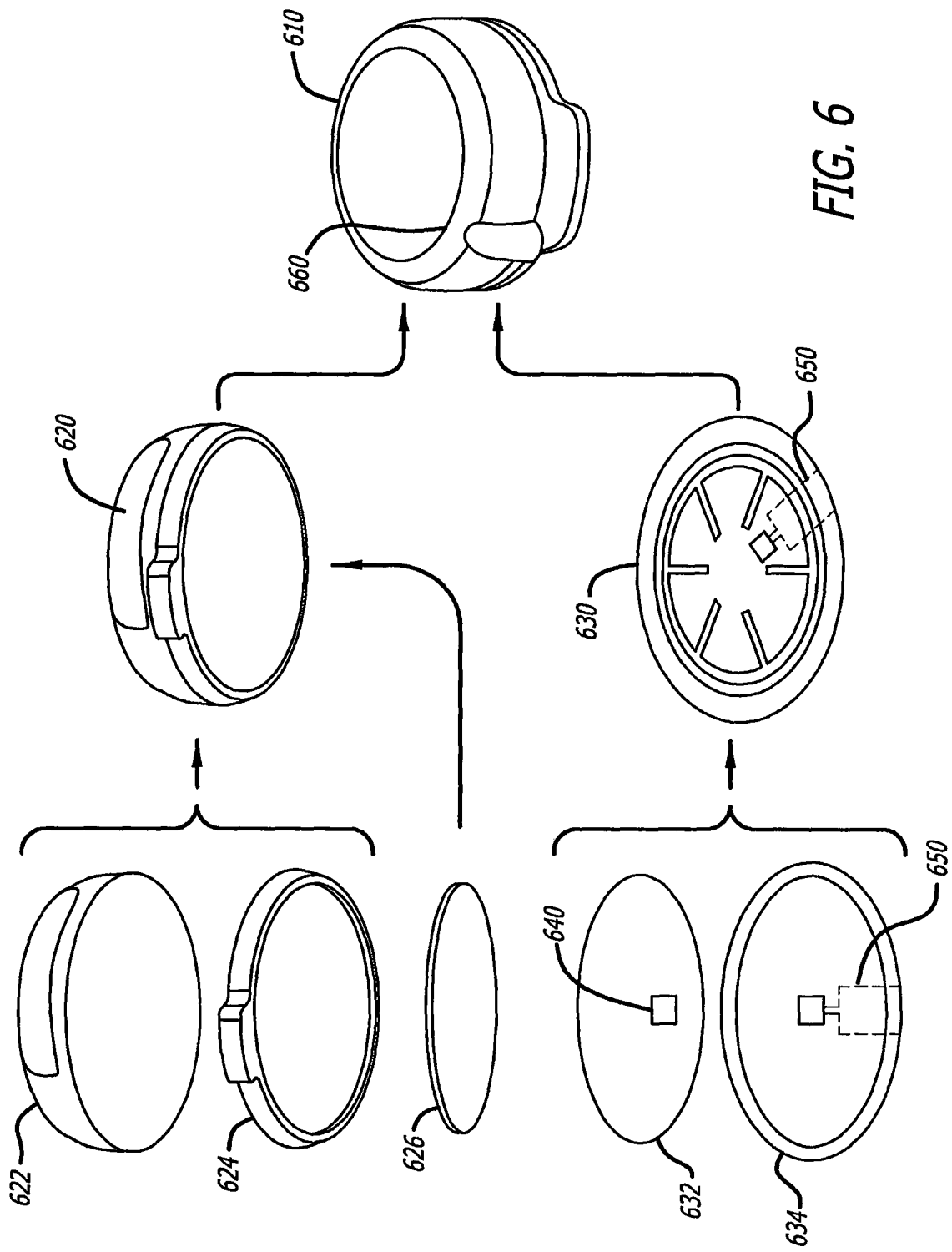
FIG. 6 shows an exemplary medical device, similar to the pump of FIG. 5a, shown in multiple exploded view, and in particular showing locations for mounting antennas in accordance with aspects of the invention.

FIG. 6 shows a medical device 610 along with an exploded view of components that comprise medical device 610 in this embodiment. The medical device 610 is assembled from a pump and base assembly 620, a skin patch assembly 630, and a hook fastener 626, and may include a pump surface mounted external antenna 660. The pump and base assembly 620 are further assembled from a pump 622 with the associated package cover, and a base 624. The skin patch assembly includes a fastener loop 632 with an antenna coupling area 640, a skin adhesive pad 634, and an external antenna 650. The antenna coupling area 640 may be a physical port, an opening, or a portion of the fastener loop 632, base 624, and/or hook fastener 626 designed to provide access or minimal barrier to an antenna coupling at each layer between the external antenna 650 and any communication circuitry inside the medical device 610. The external antenna 650 may trace the edge of the skin adhesive pad 634 for a portion of the edge, the entire edge with a break to prevent a current loop, a spiral, or any pattern on the adhesive pad 634 that provides suitable wireless performance. The medical device may include one, two, or more external antennas. The medical device 610 is shown as a device with two external antennas having both external antenna 650 and pump surface mounted external antenna 660. One may be used at a first frequency, such as 2.4 GHz while the other is used as a second frequency, such as 433 MHz.

Figure 7A:
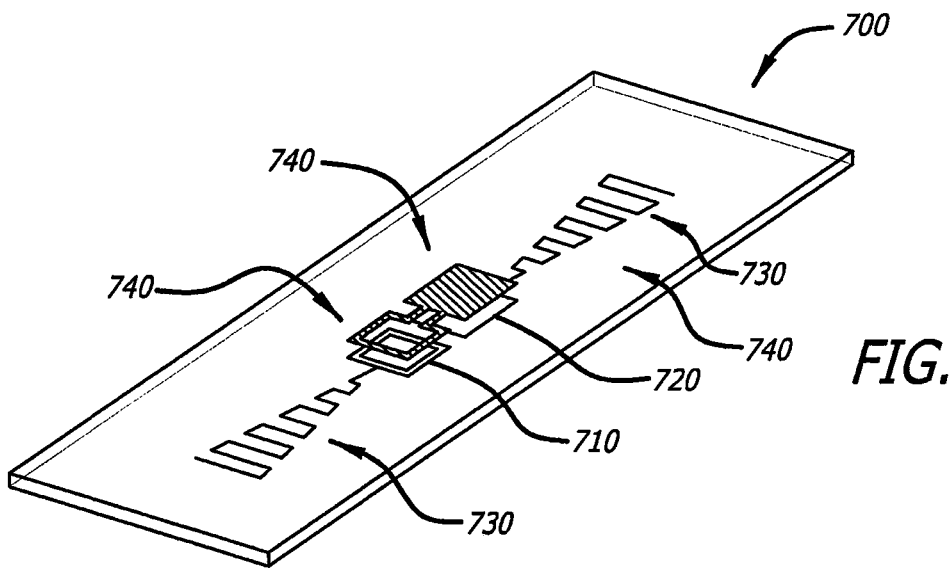
FIG. 7a presents an antenna system suitable for use in the medical device of FIG. 6 and others, having a relatively flat configuration.

FIG. 7*a* illustrates an exemplary external antenna system 700 for use with medical devices such as an insulin, pramlintide and glucagon pumps and meters or monitoring devices for materials such as glucose or other blood or patient content monitors that include a wireless transmission system. The antenna system 700 includes a primary antenna 710, a circuit 720, a secondary antenna 730, and a mounting surface 740.

Figure 7B:
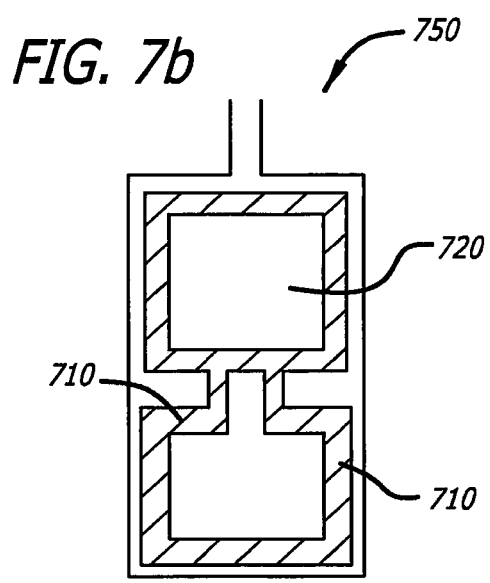
FIG. 7b illustrates an exemplary antenna design that is integrated with medical sensor system components for more efficient wireless communication of sensor data signals and other signals.

FIG. 7*b* shows the primary antenna 710, the circuit 720, and the sensor 750. The sensor 750 is coupled to the circuit 720, and may provide data related to, for example, glucose levels or levels of another blood content, drug, or analyte testable in a patient to which the sensor 750 is attached. The circuit 720 may contain additional circuitry related to sensing the material being monitored, as well as containing an internal antenna and RF communication circuits. The sensor 750 may be attached to an antenna system via a cable, or may be integrated in a single mount 740 with the rest of the antenna system 700. The circuit 720 is electrically connected to the primary antenna 710. The primary antenna 710 as shown by way of example in FIGS. 7*a* and 7*b* may be a single loop square antenna. The primary antenna 710 may additionally be a circular single loop antenna, a planar spiral antenna, a multi-loop antenna, or any other antenna capable of fulfilling a similar function, and also be made of any suitable conducting material. For example, the primary antenna 710 may be made of gold, copper, aluminum, or a printable carbon based conductor.

Figure 7C:
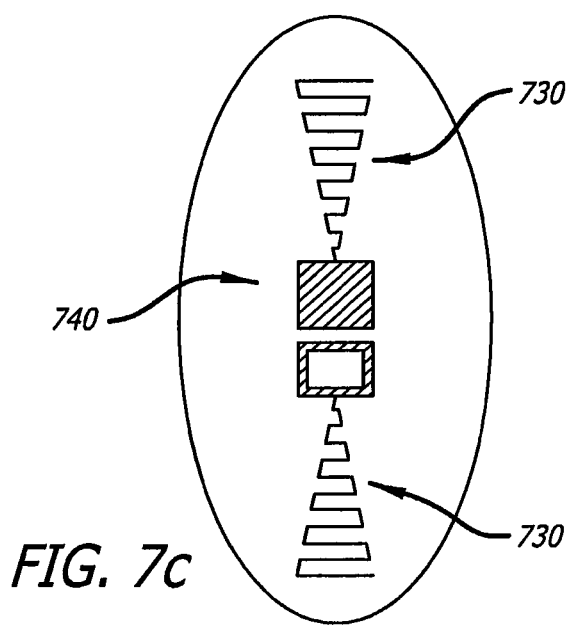

FIG. 7*c* shows a secondary antenna 730 and a mounting 740. The secondary antenna 730 is coupled to the circuit 720, either directly or via coupling with the primary antenna 710. The secondary antenna 730 as shown in FIG. 7*c* is a meandering antenna with a loop or pad at one end. The loop in the secondary antenna 730 includes a cut out to prevent formation of a current loop that will degrade the radiation power. The loop operates as a coupling antenna to improve the radiation power of the secondary antenna 730. The pad that is part of secondary antenna 730 may be used to form a capacitive coupling with a ground plane of the relevant circuit 720, as illustrated by way of example in FIG. 7*b*. The secondary antenna 730 may also be shaped like with any other arrangement of antenna that fulfill a similar function. Secondary antenna 730 may also be made of any appropriate conductive material similar to primary antenna 710.

The mounting surface 740, shown in FIGS. 7*a* and 7*c*, provides a support structure for the secondary antenna 730 as well as the circuit 720 and the primary antenna 710. In one implementation, the circuit 720 and the primary antenna 710 may be created in or on a first surface of mounting 740, and the secondary antenna 730 may be created on a second or opposite surface of the mounting 740. For example, the primary antenna may be printed on a transmitter circuit board and the secondary antenna printed on an adhesive patch. In further implementations, the secondary antenna 730 may be created on a first surface of mounting 740 and the circuit 720 and the primary antenna 710 may be created above the secondary antenna 730 on the same side of the mounting 740 with a dielectric layer between the overlapping sections to prevent electrical shorts between the various components.

The mounting 740 may be composed of flexible material to allow conformity with a surface to which the mounting 740 is located, such as a body or a curved casing. If the mounting 740 is flexible, the material that makes up the primary antenna 710 and the secondary antenna 730 will either be sufficiently flexible to avoid cracking or snapping when the mounting 730 bends, or will be supported by additional support structures to prevent bending that would cause such damage. In one alternative implementation, the primary antenna 710 and the circuit 720 are created on an inflexible dielectric which is mounted to a flexible mounting 740 having a flexible implementation of the secondary antenna 730 on one side. The opposite side of the mounting 740 is covered with an adhesive material that allows the mounting 740 to be attached to a curved surface while still connected to a primary antenna 710 and/or other circuitry (i.e., circuit 720), which may be supported, e.g., by an inflexible dielectric element.

Figure 7D:
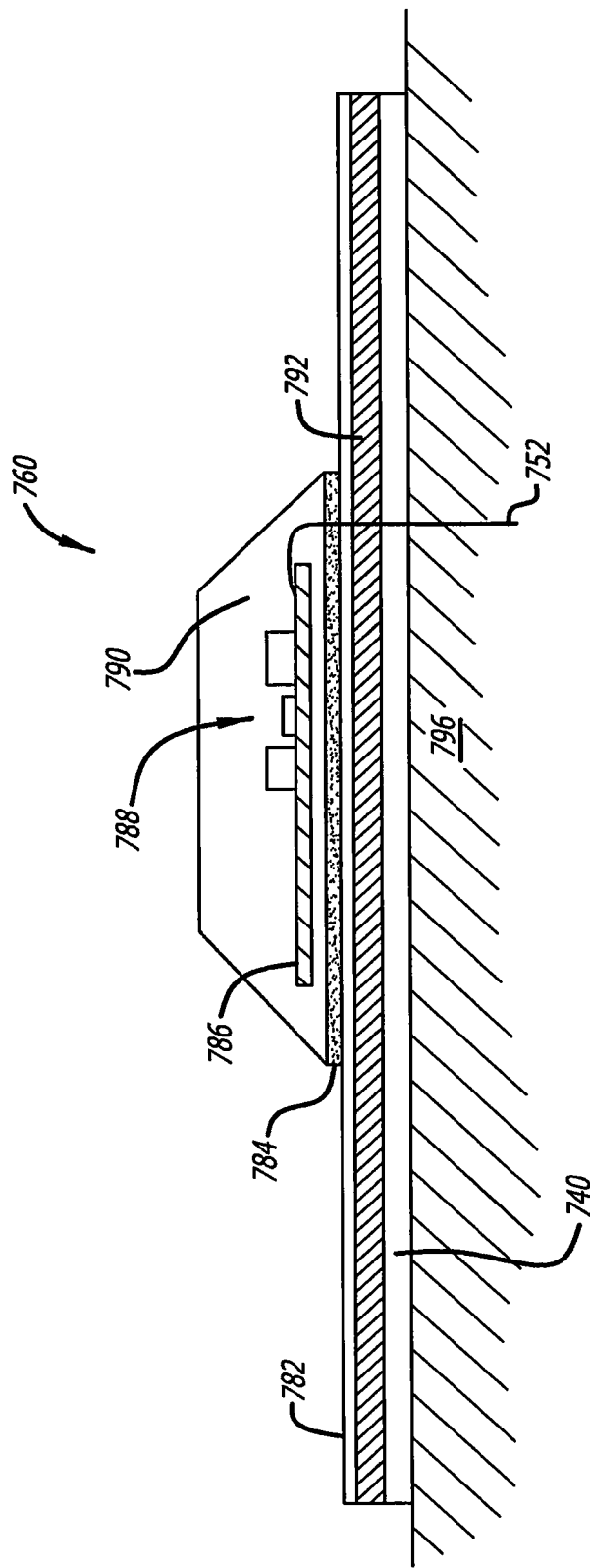
FIG. 7d presents an antenna and mounting system for mounting the antenna at or near the skin of a patient, showing the various layers for manufacturing purposes, in this case the antenna being fully integrated with a glucose sensor.

FIG. 7d illustrates the structure of an embodiment consistent with certain aspects related to the present invention. Referring to FIG. 7d, a system 760 is shown mounted to the skin 796 of a user. A mounting 740 is attached directly to the skin as an adhesive patch layer, and may be similar to the mounting 740 of FIG. 7c. The mounting 740 is attached to a bottom surface of a thin film substrate 792 which contains a secondary antenna such as the secondary antenna 730 of FIG. 7c, within a printed conductive layer 782. A transmitter adhesive layer 784 is attached to the top surface of the printed conductive layer 782, and attaches the encapsulated transmitter 790 to the mounting 740 through the other layers. The encapsulated transmitter 790 includes electronic components 788 and a printed circuit board 786. The printed circuit board 786 may contain a primary antenna such as the primary antenna 710 of FIG. 7a. The sensor tip 752 may be a portion of a sensor such as the sensor 750 of FIG. 7a. The sensor tip 752 is inserted into the skin 796 of the user, and is attached to the printed circuit board 786 via the sensor either through a via or around the edge of the substrate and mounting layers.

Figure 8A:
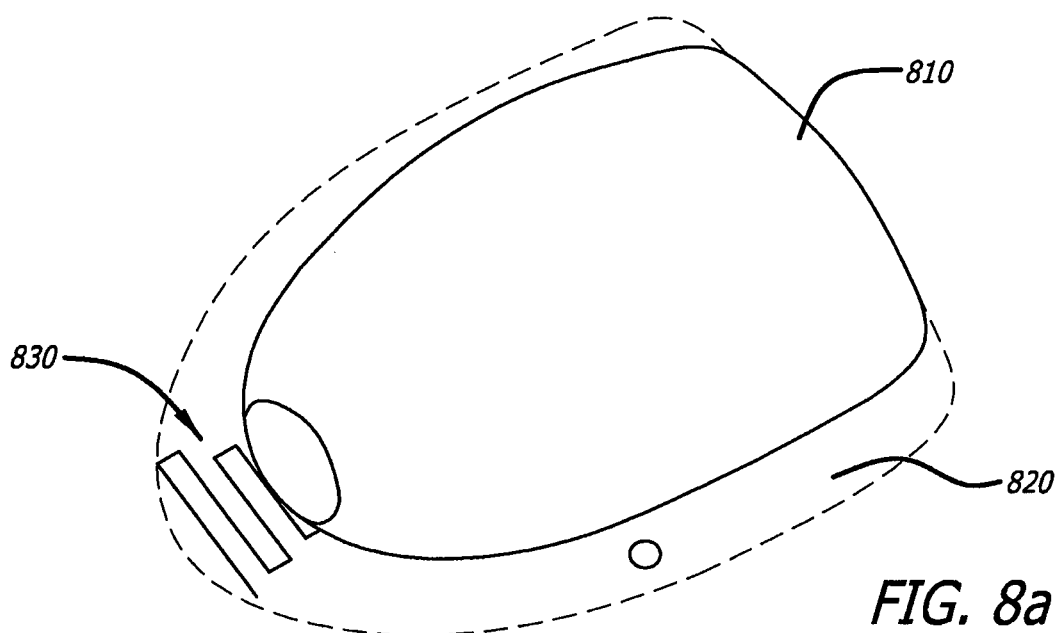
FIG. 8a is a top view of a medical device, in this case a diabetes medication pump similar to that of FIG. 6, showing the positioning of an external antenna on the adhesive layer.
Figure 8B:
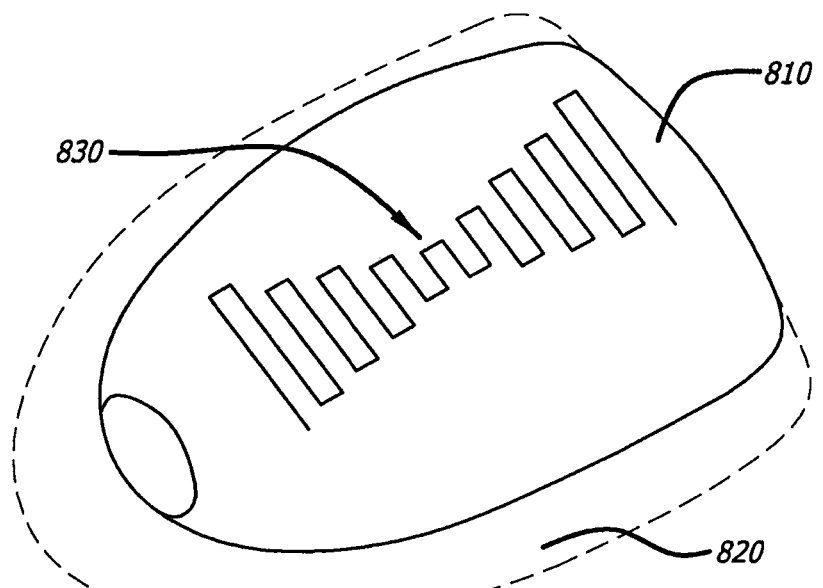
FIG. 8b is also a top view of the medical device of FIG. 8a showing the mounting of an external antenna on the upper external surface of the case rather on the adhesive layer.

FIG. 8a illustrates the structure of certain components of an embodiment consistent with certain aspects related to the present invention. Referring to FIG. 8a, a medical device 810 is shown. The medical device 810 is attached to an adhesive layer 820 that includes an antenna 830. The antenna 830 may be printed on a surface, embedded within a surface, or woven into a woven material layer of the adhesive layer 820. The antenna 830 may be electrically connected to RF transmission circuitry contained within the medical device 810 through an electrical connection contained in the adhesive layer 820. As described above, the adhesive layer 820 may be used to attach the medical device 810 to a user. Persons of ordinary skill in the art will appreciate that the system is exemplary, and that alternative structures consistent with the aspects related to the present invention are possible. For example, FIG. 8b illustrates one alternative, wherein the antenna 830 is positioned on the outside case of the medical device 820. The medical device 810 is still attached to an adhesive layer 820 that may be used to attach the medical device 810 to a user. The antenna 830 may be electrically connected to communication circuitry inside the medical device 810 by an electrical path through the case of the medical device 810.

Use of external packaging such as shown in FIGS. 6 and 8b, or an adhesive mounting patch such as shown in FIGS. 7 and 8a with a thin film printed antenna or other antenna configurations offer superior radio frequency performance for wirelessly enabled pumps as opposed to internal antenna or single wire tube attached antenna.

The embodiments set forth in the above descriptions do not represent all embodiments consistent with the claimed invention. Instead, they are merely some examples consistent with certain aspects related to the invention. While only the presently preferred embodiments have been described in detail, as will be apparent to those skilled in the art, modifications and improvements may be made to the device disclosed herein without departing from the scope of the invention. Accordingly, it is not intended that the invention be limited, except as by the appended claims.

We claim:

1. A medical device configured to monitor an analyte level of a user, the medical device comprising:
   a mounting surface configured to support a transmitter circuit board, electronic circuitry, a first antenna, and a second antenna; and
   a sensor coupled with the electronic circuitry, the sensor configured to sense an analyte level in a bodily fluid of the user and to provide sensor data to the electronic circuitry,
       wherein the first antenna and the second antenna are electrically coupled with the electronic circuitry,
       wherein the first antenna is disposed in the transmitter circuit board, and
       wherein the second antenna is located above the first antenna on a same side of the transmitter circuit board as the electronic circuitry.

2. The medical device of claim 1, wherein the first antenna comprises a copper material.

3. The medical device of claim 1, wherein the first antenna comprises a circular multi-loop antenna.

4. The medical device of claim 1, wherein the first antenna is further disposed in at least one layer of the transmitter circuit board.

5. The medical device of claim 1, wherein the electronic circuitry comprises radio frequency (RF) communication circuitry coupled with the second antenna.

6. The medical device of claim 1, wherein the second antenna comprises a meandering pattern.

7. The medical device of claim 1, wherein the second antenna includes a pad located at an end portion of the second antenna, wherein the pad is coupled with the transmitter circuit board.

8. The medical device of claim 1, wherein the mounting surface includes an adhesive surface configured to be adhered to a skin surface of the user.

9. The medical device of claim 1, wherein the sensor comprises a sensor tip configured to be inserted under a skin layer of the user.

10. The medical device of claim 1, wherein the sensor comprises a proximal portion configured to be coupled with the electronic circuitry.

11. The medical device of claim 1, wherein the sensor comprises a glucose sensor.

12. The medical device of claim 1, wherein the first antenna is configured to wirelessly communicate at a first frequency, and the second antenna is configured to wirelessly communicate at a second frequency different from the first frequency.

13. A medical device configured to monitor an analyte level of a user, the medical device comprising:
   a sensor coupled with electronic circuitry, wherein the sensor is configured to sense an analyte level in a bodily fluid of the user and to provide sensor data to the electronic circuitry; and
   a first antenna and a second antenna, both of which are coupled with the electronic circuitry,
       wherein the first antenna comprises a circular multi-loop antenna disposed in a transmitter circuit board, and wherein the second antenna comprises a meandering pattern and is located above the first antenna on a same side of the transmitter circuit board as the electronic circuitry.

14. The medical device of claim 13, wherein the first antenna is configured to wirelessly communicate at a first frequency, and the second antenna is configured to wirelessly communicate at a second frequency different from the first frequency.

15. The medical device of claim 13, wherein the electronic circuitry comprises radio frequency (RF) communication circuitry coupled with the second antenna.

16. The medical device of claim 13, wherein the sensor comprises a sensor tip configured to be inserted under a skin layer of the user.

17. The medical device of claim 13, wherein the sensor comprises a proximal portion configured to be coupled with the electronic circuitry.

18. The medical device of claim 13, wherein the sensor comprises a glucose sensor.

19. The medical device of claim 13, further comprising a mounting surface including an adhesive surface configured to be adhered to a skin surface of the user.

20. The medical device of claim 13, wherein the second antenna includes a pad located at an end portion of the second antenna, wherein the pad is coupled with the transmitter circuit board.

* * * * *